US012618823B2

(12) United States Patent
Tsang et al.

(10) Patent No.: US 12,618,823 B2
(45) Date of Patent: May 5, 2026

(54) METHOD OF QUANTIFYING MICROPLASTIC MASS

(71) Applicant: The Education University of Hong Kong, Tai Po (HK)

(72) Inventors: Yiu Fai Tsang, Tai Po (HK); Yan Laam Cheng, Tai Po (HK); Ziying Li, Tai Po (HK)

(73) Assignee: The Education University of Hong Kong, Tai Po (HK)

( * ) Notice: Subject to any disclaimer, the term of this patent is extended or adjusted under 35 U.S.C. 154(b) by 610 days.

(21) Appl. No.: 18/173,178

(22) Filed: Feb. 23, 2023

(65) Prior Publication Data

US 2025/0052735 A1     Feb. 13, 2025

(51) Int. Cl.
*G01N 33/18*      (2006.01)
*G01N 1/40*       (2006.01)

(52) U.S. Cl.
CPC ....... *G01N 33/1846* (2013.01); *G01N 1/4022* (2013.01); *G01N 1/4044* (2013.01); *G01N 1/4077* (2013.01); *G01N 2001/4027* (2013.01); *G01N 2001/4088* (2013.01)

(58) Field of Classification Search
CPC ....... A61K 31/40; A61P 35/00; C07D 211/18; C07D 401/12; C07D 221/18; Y02P 20/582; G01N 1/4022; G01N 1/4044; G01N 1/4077; G01N 1/44; G01N 2001/4027; G01N 2001/4083; G01N 2001/4088; G01N 33/1846
See application file for complete search history.

(56) References Cited

U.S. PATENT DOCUMENTS

2020/0408734 A1*  12/2020  Ferrante ............... G01N 1/4077

FOREIGN PATENT DOCUMENTS

CN        119534068 A  *  2/2025  ......... G01N 21/3577
KR       20230016993 A  *  2/2023  ......... G01N 33/1846
WO   WO-2021163821 A1 *  8/2021  ......... G01N 33/1846

OTHER PUBLICATIONS

Liu (WO-2021163821-A1) English Translation (Year: 2025).*
Guo (CN-119534068-A) English Translation (Year: 2025).*
Kim (KR-20230016993-A) English Translation (Year: 2025).*

* cited by examiner

*Primary Examiner* — Jennifer Wecker
*Assistant Examiner* — Jonathan Bortoli
(74) *Attorney, Agent, or Firm* — FASKEN MARTINEAU DUMOULIN LLP; Kimberly A. Peaslee

(57) ABSTRACT

A method of quantifying microplastic mass in a sample composition, including the steps of pre-treating the sample composition to remove non-microplastic organic matter and extract microplastics thereby providing a pre-treated sample composition, measuring the organic carbon content of a microplastic polymer in the pre-treated sample composition using total organic carbon (TOC) analysis, and quantifying the microplastic mass in the sample composition according to the organic carbon content of the microplastic polymer.

17 Claims, 12 Drawing Sheets

/ 105

Pre-treat a sample composition to remove non-microplastic organic matter and extract microplastics and thereby provide a pre-treated sample composition
100

Measure the organic carbon content of a microplastic polymer in the pre-treated sample composition using total organic carbon analysis
110

Quantify the microplastic mass in the sample composition according to the organic carbon content of the microplastic polymer
120

515

500

With drying

500

510

510

510

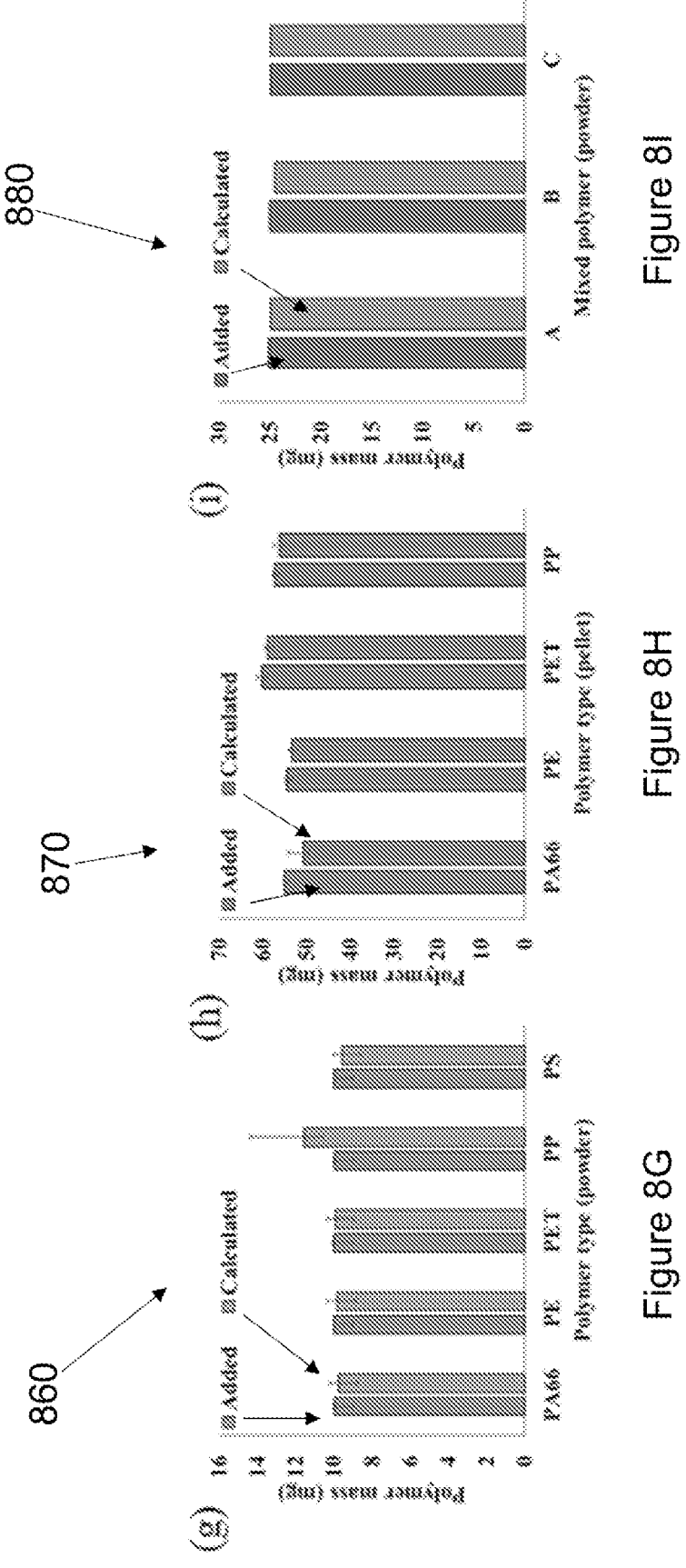

METHOD OF QUANTIFYING MICROPLASTIC MASS

TECHNICAL FIELD

This invention relates to a method of quantifying microplastic mass in a sample composition, in particular the present disclosure is directed to a method of quantifying microplastic mass in a sample composition using total organic carbon (TOC) analysis.

BACKGROUND

The durable, lightweight, low cost and adaptable nature of plastics has led to their widespread use commercially and in some form in almost all households. However, the widespread use of plastics has resulted in the accumulation of plastic waste in the environment. The rising global population has contributed to a large and continually growing amount of plastic waste generated every day. Plastic waste is broken down into microplastics and these microplastic pollutants have permeated the natural ecosystem, being present in soil, rivers, and oceans, and has caused widespread environmental problems. The presence of microplastics within the food chain is also increasing and can harm ecosystems and human health.

The persistence of microplastics in the natural environment and its effects on organisms are the subject of environmental research and scientific interest. To study and understand the abundance, location and effects of microplastics in the natural ecosystem, reliable and effective methods of monitoring microplastics are desired.

SUMMARY OF THE INVENTION

According to a first aspect of the invention, there is provided a method of quantifying microplastic mass in a sample composition, including the steps of: pre-treating the sample composition to remove non-microplastic organic matter and extract microplastics thereby providing a pre-treated sample composition, measuring the organic carbon content of a microplastic polymer in the pre-treated sample composition using total organic carbon (TOC) analysis, and quantifying the microplastic mass in the sample composition according to the organic carbon content of the microplastic polymer. For example, the method of the invention is used to monitor microplastic pollutants in wastewater, pond water or sludge for environmental pollution assessments.

In the method of the invention, total organic carbon (TOC) analysis is used to quantify microplastic mass in a sample composition. The microplastic polymer may be, for example, a single polymer or a mixture of polymers and can be in the form of a powder or a pellet. In an example embodiment, the microplastic polymer includes polyamide 66 (PA 66), polyethylene (PE), polyethylene terephthalate (PET), polypropylene (PP), polystyrene combination thereof.

Existing analytical techniques used for microplastic quantification are time consuming, typically taking several days to identify microplastic polymer types and determine the microplastic mass contents. The accuracy and viability of these existing analytical techniques may also be hindered by the size, shape, presence of biofilm or other organic pollutants on the microplastic, and they often require the use of expensive analytical instruments to conduct analysis of the small microplastics. Advantageously, the accuracy of the method of the invention is not affected by variable factors of microplastic characteristics such as the broad size range of the microplastic, microplastic polymer types and additives, or different shapes of microplastics. The method of the invention is also quick and inexpensive, only requiring infrastructure commonly available in environmental testing laboratories, thereby saving 75% of sample pre-treatment time and 60% of extraction costs. Further, the invention reliably provides mass-based concentrations of microplastic polymers in sample compositions with different viscosities, i.e., liquid samples or sludge samples, with high recovery rates of the microplastic polymers in the liquid and sludge samples of over 98%.

In a preferred embodiment, pre-treating the sample composition includes the steps of: digesting the sample composition using a pre-determined digestion reagent for a pre-determined digestion to duration remove non-microplastic organic matter, extracting the microplastic polymer from the sample composition by density separation to produce a microplastic layer, filtering the microplastic layer through a filter such that the microplastic polymer is captured in the filter, and drying the filter with the captured microplastic polymer for a pre-determined drying time at a pre-determined drying temperature in preparation for total organic carbon (TOC) analysis.

Pre-treatment of the sample composition removes undesired non-microplastic organic matter or impurities to ensure the accuracy of the microplastic quantification using total organic carbon (TOC) analysis. Sample composition pre-treatment also extracts or isolates microplastic polymers from the sample composition prior to TOC analysis. Pre-treatment of the sample composition provides a low-cost, fast, reliable and simple way of eliminating undesired organic carbon content in sample compositions without the need for expensive reagents or instruments or time-consuming and cumbersome pre-treatment methods.

In an example embodiment, during pre-treatment, the pre-determined digestion reagent is selected from the group including 30% hydrogen peroxide, wet peroxide oxidation (WPO), a mixture of acids, and the pre-determined digestion duration is between 2 hours to 24 hours. Preferably, the pre-determined digestion duration is 2 hours, 4 hours, 6 hours, 8 hours or 24 hours. In a preferred embodiment, the pre-determined digestion duration is 2 hours, and the digestion reagent is 30% hydrogen peroxide and the digestion is performed at a preferred temperature of 45° C. Most preferably, digestion is performed on a heat plate at a temperature of 45° C. for 2 hours and the sample composition is stirred at a rate of 200-300 rotations per minute. The digestion step utilises inexpensive reagents and a simple method to beneficially remove non-microplastic organic matter to ensure the accuracy of the TOC analysis of the sample composition.

In an example embodiment, the microplastic polymer is extracted from the sample composition after the addition of filtered sodium bromide, and density separation is performed at 25° C. for at least 2 hours.

In a most preferred embodiment, the pre-treatment includes a first operation mode for sample compositions with high organic content, and a second operation mode for sample compositions with low organic content. In the first operation mode, sample compositions with high organic content, for example, sludge or solid-rich samples, undergo density separation before digestion. This modified operation mode advantageously achieves higher recovery rates of microplastic polymer mass. In the second operation mode, sample compositions with low organic content, for example, liquids with low viscosity, undergo digestion before density separation during pre-treatment.

In an example embodiment, the ratio of digestion reagent to sample composition having a low organic content is 1:1. In a further example embodiment, the ratio of digestion reagent to sample composition having a high organic content is 2:1.

In a preferred embodiment, the microplastic layer is filtered through a 0.4-μm glass fiber filter under vacuum.

In another example embodiment, during pre-treatment, the filter with the captured microplastic polymer is put in a pre-treated ceramic boat and dried in an oven. For example, the pre-determined drying time is overnight. Preferably, the pre-determined drying time is between 2 hours and 8 hours and the pre-determined drying temperature is 60° C.

In all embodiments, the total organic carbon (TOC) analysis is performed using a TOC analyzer. In an example embodiment, the pre-treated sample, for example the ceramic boat with the filter with the captured microplastic polymer, is inserted into a TOC analyzer with a solid-sample combustion unit. Preferably, the pre-treated sample composition is inserted into the TOC analyzer and combusted at 900° C. to measure the carbon mass of the microplastic polymer.

In a most preferred embodiment, the microplastic mass is quantified according to the carbon content of the microplastic polymer and a measured carbon mass from the TOC analyzer.

In particular, an advantageous feature of the invention is that the method of the invention is applicable not only to the microplastic quantification of a single polymer in powder or pellet forms, but also microplastic polymers in various compositions as would be present in real-life samples. The invention illustrates the successful application of the total organic carbon (TOC) analysis method for microplastic quantification for samples with mixed polymers. The experimental results achieved showed a high recovery rate of polymer mass, thus beneficially providing a quick, inexpensive, accurate, and reliable method of monitoring microplastic mass in a range of different sample compositions.

BRIEF DESCRIPTION OF THE DRAWINGS

Embodiments of the present invention will now be described, by way of example, with reference to the accompanying drawings in which.

4

Figures 6A, 6B:
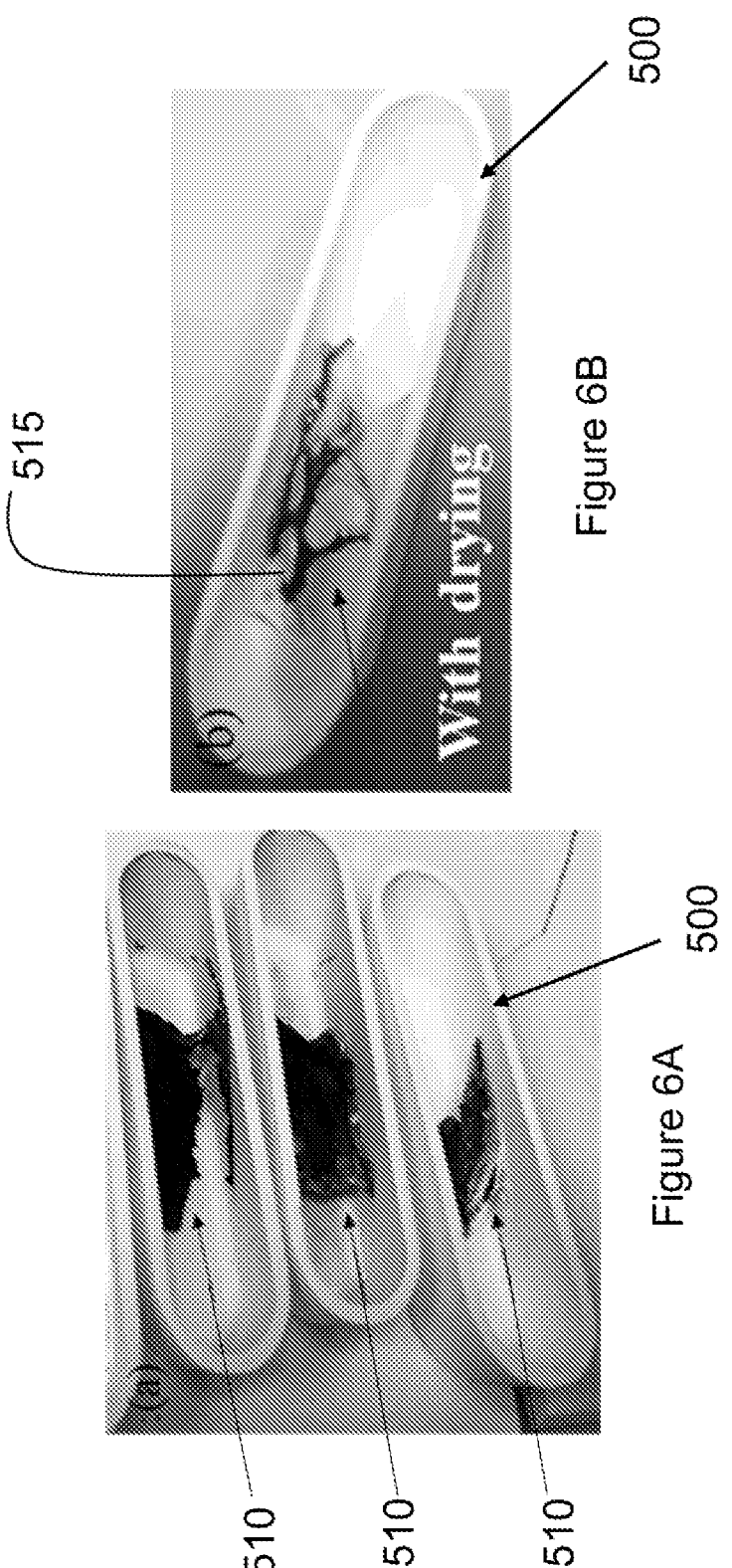

FIG. 6A is a photograph of ceramic boats with partly dried sample compositions after total organic carbon (TOC) analysis in accordance with an example embodiment.

FIG. 6B is a photograph of a ceramic boat with a dried sample composition after total organic carbon (TOC) analysis in accordance with an example embodiment.

Figure 7C:
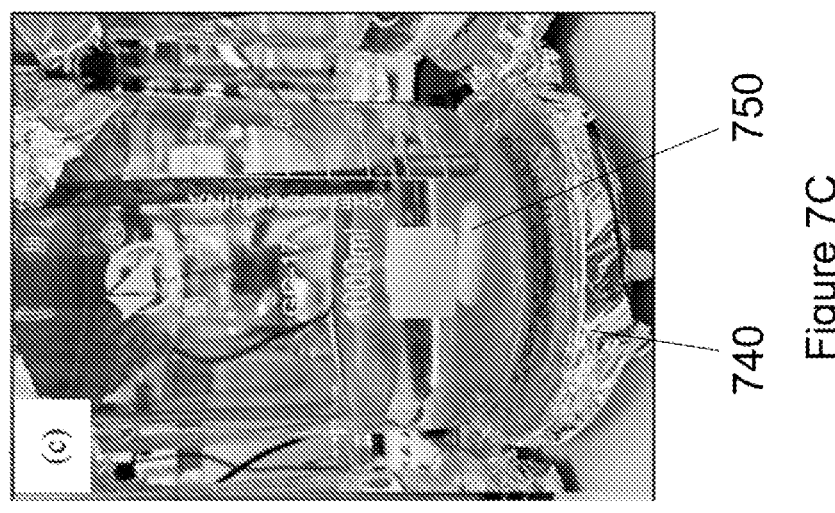
Figure 7B:
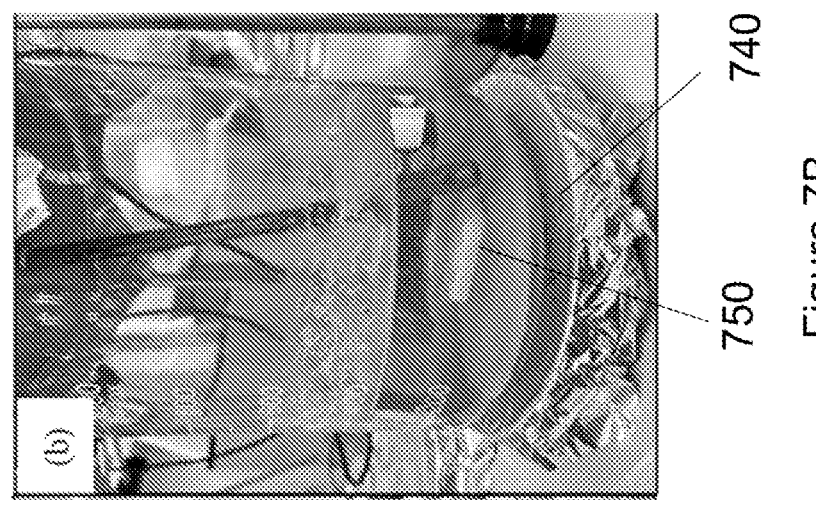
Figure 7A:
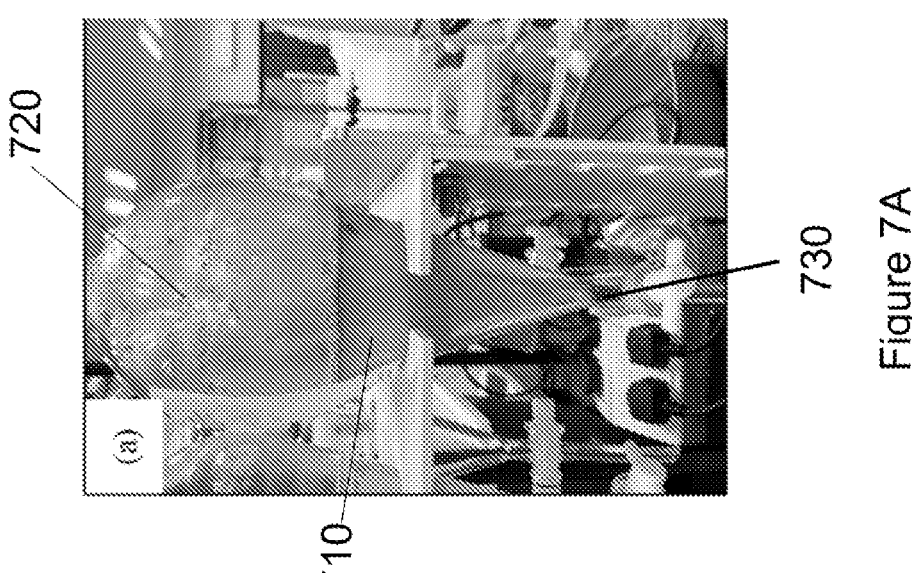

FIG. 7A is a photograph showing density separation of the sample composition to separate microplastic polymer from impurities during pre-treatment of the sample composition in accordance with an example embodiment.

FIG. 7B is a photograph of the sample composition after density separation and before digestion using 30% hydrogen peroxide in accordance with an example embodiment.

FIG. 7C is a photograph of the sample composition after 2-hour digestion with 30% hydrogen peroxide in accordance with an example embodiment.

Figure 7D:
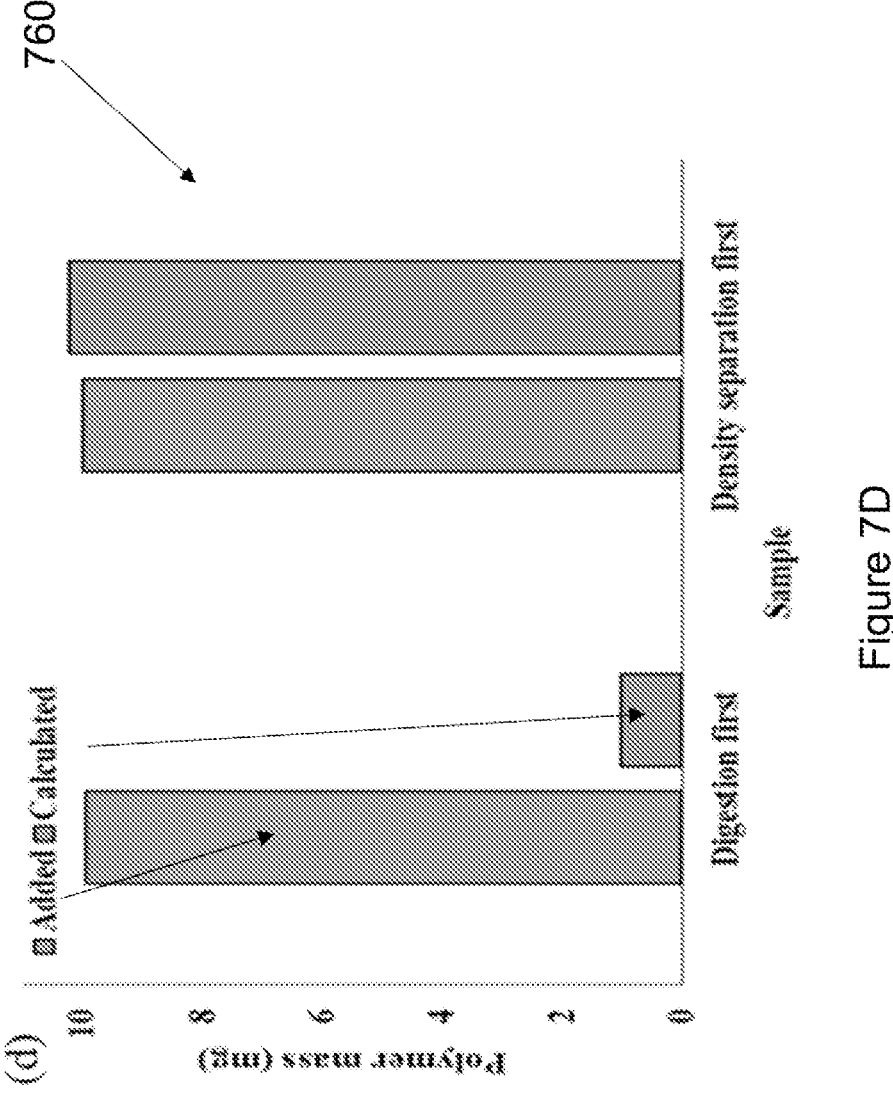

FIG. 7D is a graph comparing the microplastic polymer mass quantified in a sample composition with high organic content with the microplastic polymer mass initially added for a first operation mode and a second operation mode during pre-treatment in accordance with an example embodiment.

Figures 8A, 8B, 8C:
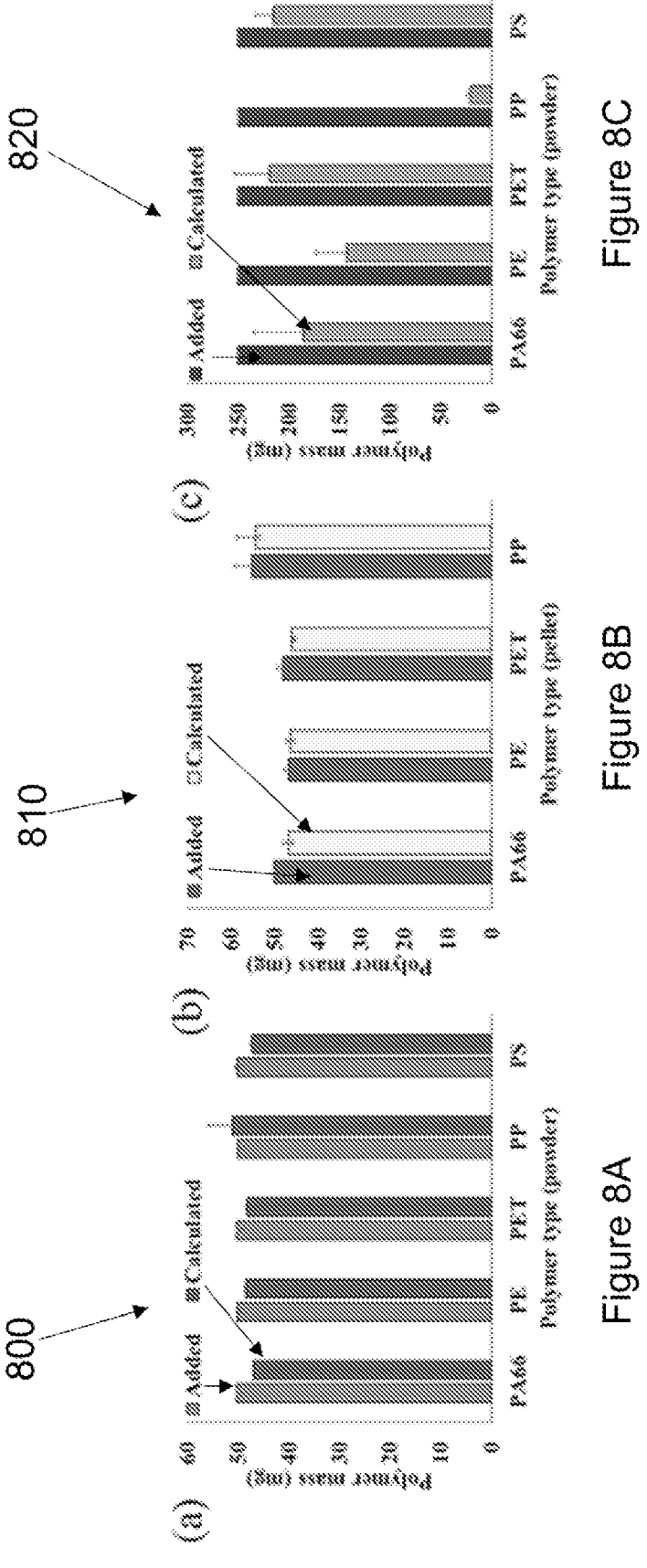

FIG. 8A is a graph illustrating the quantification of microplastic mass using a total organic carbon analyzer of a sample composition with microplastic polymer in powder form in accordance with an example embodiment.

FIG. 8B is a graph illustrating the quantification of microplastic mass using a total organic carbon analyzer of a sample composition with microplastic polymer in pellet form in accordance with an example embodiment.

FIG. 8C is a graph illustrating the quantification of microplastic mass using a total organic carbon analyzer of a synthetic liquid sample composition with microplastic polymer in powder form in accordance with an example embodiment.

Figures 8D, 8E, 8F:
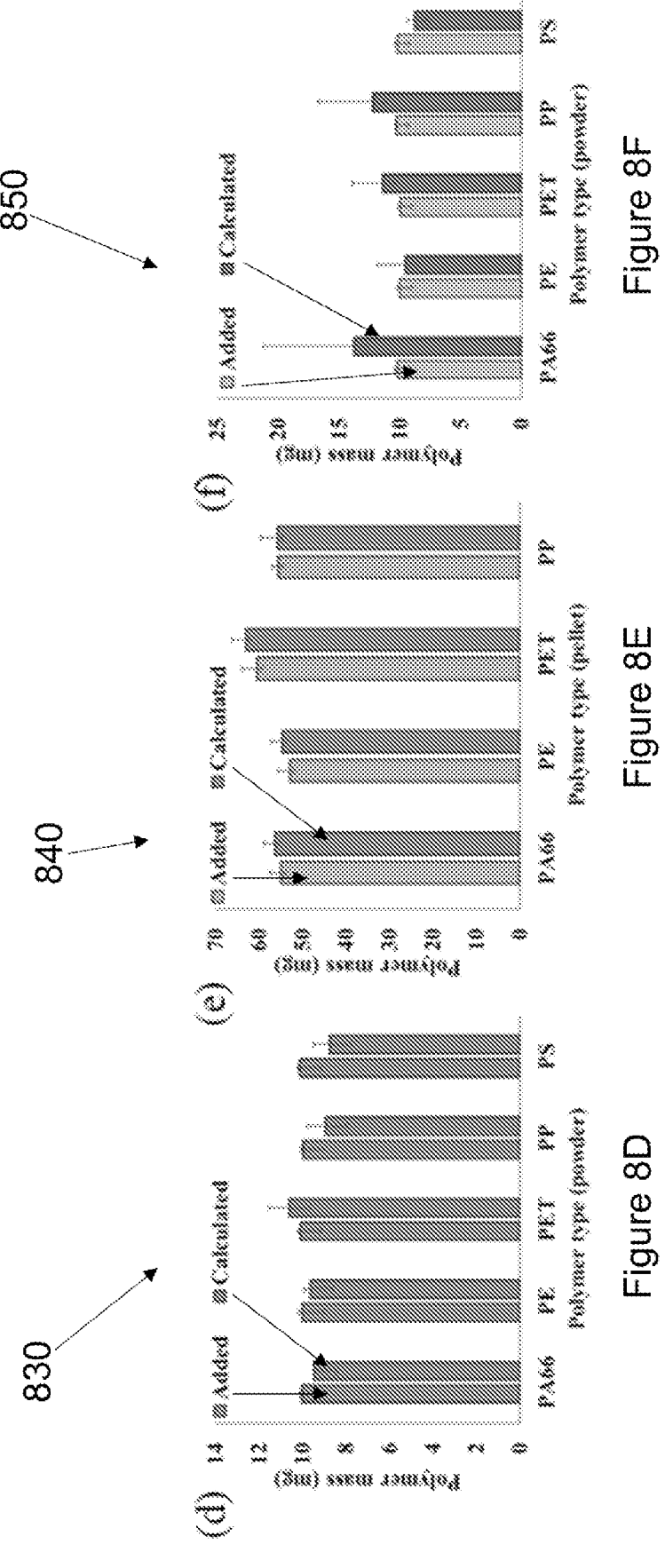

FIG. 8D is a graph illustrating the quantification of microplastic mass using a total organic carbon analyzer of a pond water sample composition with microplastic polymer in powder form in accordance with an example embodiment.

FIG. 8E is a graph illustrating the quantification of microplastic mass using a total organic carbon analyzer of a pond water sample composition with microplastic polymer in pellet form in accordance with an example embodiment.

FIG. 8F is a graph illustrating the quantification of microplastic mass using a total organic carbon analyzer of a synthetic sludge sample composition with microplastic polymer in powder form in accordance with an example embodiment.

FIG. 8G is a graph illustrating the quantification of microplastic mass using a total organic carbon analyzer of a dewatered sludge sample composition from a water treatment works with microplastic polymer in powder form in accordance with an example embodiment.

FIG. 8H is a graph illustrating the quantification of microplastic mass using a total organic carbon analyzer of a dewatered sludge sample composition from a water treatment works with microplastic polymer in pellet form in accordance with an example embodiment.

FIG. 8I is a graph illustrating the quantification of microplastic mass using a total organic carbon analyzer of a mixed polymer sample composition with microplastic polymer in powder form in accordance with an example embodiment.

DETAILED DESCRIPTION OF THE PREFERRED EMBODIMENT

The widespread utilisation of plastics worldwide has resulted in the growing accumulation of plastic waste, among these are microplastics. Microplastics can persist and migrate in various natural environments, including air, soil, oceans and freshwater. Their small size and abundance mean they are easily ingested by organisms and spread across all levels of the food chain, and microplastics have been identified in environmental samples in aerosols, sediments, soils and water from various habitats. Exposure to microplastics can cause severe health concerns. Therefore, it is detect, important to identify and quantify microplastics in environmental samples to monitor and map the abundance of microplastic pollutants in various environments and assess and prevent potential damage to organisms.

Figure 1:
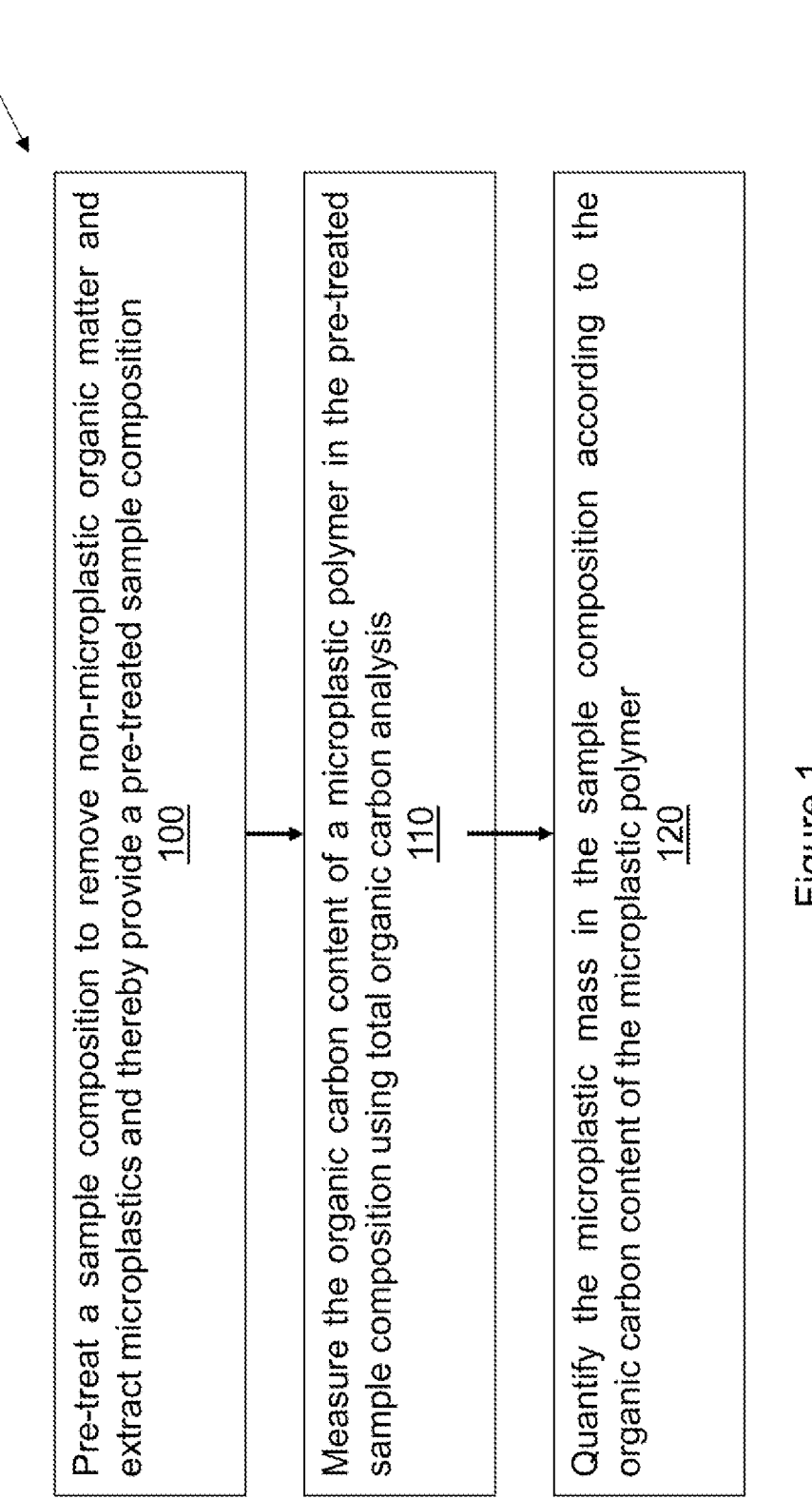
FIG. 1 is a method of quantifying microplastic mass in a sample composition using total organic carbon (TOC) analysis in accordance with an example embodiment.

With reference to FIG. 1, an embodiment of the present invention is illustrated. This embodiment is arranged to provide a method 105 of quantifying microplastic mass in a sample composition, comprising the steps of: pre-treating 100 the sample composition to remove non-microplastic organic matter and extract microplastics and provide a pre-treated sample composition, measuring 110 the organic carbon content of a microplastic polymer in the pre-treated sample composition using total organic carbon (TOC) analysis 350, and quantifying 120 the microplastic mass in the sample composition according to the organic carbon content of the microplastic polymer. The claimed microplastic mass quantification method can advantageously be used to accurately and reliably monitor the presence, abundance, and mass of microplastics in different environments as a valuable assessor of the pollution levels of microplastics in different environments. The claimed method may be used in the quantification of microplastic polymers such as polyamide 66, polyethylene (PE), polyethylene terephthalate, polypropylene, polystyrene, or a combination thereof. Further, the microplastic polymer may be a single polymer or a mixture of polymers and may be in the form of a powder or a pellet. The claimed method may be used to quantify the microplastic mass in a sample composition such as wastewater, pondwater or sludge. FIGS. 8A-8I show the quantification of microplastics using a TOC analyzer 350. FIG. 8A illustrates a graph 800 showing high microplastic polymer mass recovery rates of polymer in powder form. FIG. 8B illustrates a graph 810 showing high microplastic polymer mass recovery rates in of polymer in pellet form. FIG. 8C illustrates a graph 820 showing high microplastic polymer mass recovery rates in a synthetic liquid sample with polymer in powder form. FIG. 8D illustrates a graph 830 showing high microplastic polymer mass recovery rates in a pond water sample with polymer in powder form. FIG. 8E illustrates a graph 840 showing high microplastic polymer mass recovery rates in a pond water sample with polymer in pellet form. FIG. 8F illustrates a graph 850 showing high microplastic polymer mass recovery rates in synthetic sludge sample composition with polymer in powder form. FIG. 8G illustrates a graph 860 showing high microplastic polymer mass recovery rates in dewatered sludge sample from water treatment works with polymer in powder form. FIG. 8H illustrates a graph 870 showing high microplastic polymer mass recovery rates in dewatered sludge sample from water treatments works with polymer in pellet form. FIG. 8I illustrates a graph 880 showing high microplastic polymer mass recovery rates of mixed polymer in powder form.

In the claimed method of the invention, total organic carbon (TOC) analysis is applied to quantify microplastic mass. Currently, the most common technique for quantifying microplastics is identifying polymer types and visual counting with an optical microscope, an approach that is labour intensive and prone to human error. Spectroscopy, including Fourier transform infrared spectroscopy (FT-IR) and Raman spectroscopy, are the most commonly applied techniques for identifying polymers collected through visual sorting. These are time-intensive analyses for which several days are required to complete quantification and qualification of microplastics in a single sample. They also require advanced equipment which can be costly and increase operation costs. A further drawback of these analytical techniques is that the spectroscopy methods may be hindered by factors such as the size of the microplastic polymers, shape of the microplastic polymers, or the presence of biofilm or other organic pollutants on the surface of microplastics. Pyrolysis-gas chromatography/mass spectrometry (Py-GC/MS) and gas chromatography/mass spectrometry (GC/MS) are also used in the quantification of microplastics. The quantification of microplastics through Py-GC/MS requires a complex process which requires reagent-intensive and labour-intensive analyses. GC/MS analysis also involves a solvent-intensive and labour-intensive method.

The claimed method of microplastic quantification using TOC analysis is not limited by the characteristics of microplastics, such microplastic polymer size, as microplastics are quantified according to their carbon mass content. The method also does not require expensive solvents, as is the case for existing analytical techniques, and offers a low-cost, fast, reliable and simple method of microplastic quantification.

The claimed method includes pre-treatment 205 of the sample composition. The pre-treatment steps facilitate a high recovery rate of microplastic quantification through removal of impurities (including impurities or other non-microplastic organic matter) 730 that directly affects the carbon content of the sample composition. The sample pre-treatment as disclosed can effectively eliminate undesired non-microplastic organic carbon content in a sample, thereby eschewing the need for expensive solvents or reagents. Thus, removal of impurities, including non-plastic organic matter 730 is a crucial step to ensure the accuracy of the microplastic mass quantified using TOC analysis 350. Additionally, digestion reagent type, digestion duration and digested sample dryness are important factors that affect TOC analysis effectiveness and efficiency and the claimed method takes these factors into consideration and ensure optimal pre-treatment conditions.

Figure 2:
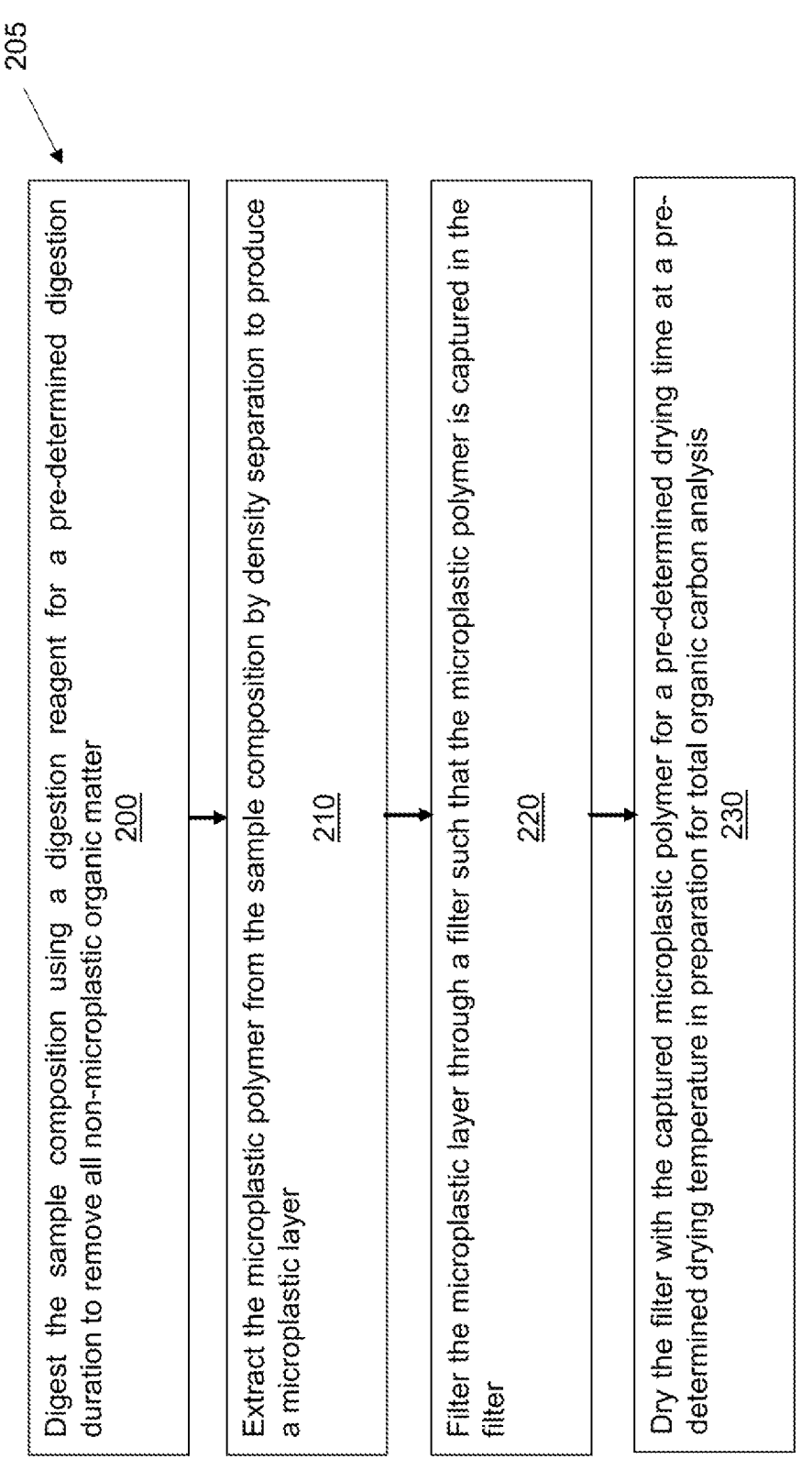
FIG. 2 is a method of pre-treating a sample composition in preparation for total organic carbon (TOC) analysis in accordance with an example embodiment.

With reference to FIG. 2, sample pre-treatment 205 involves four steps, including digestion 200, density separation 210, filtration 220 and drying 230.

Figure 4:
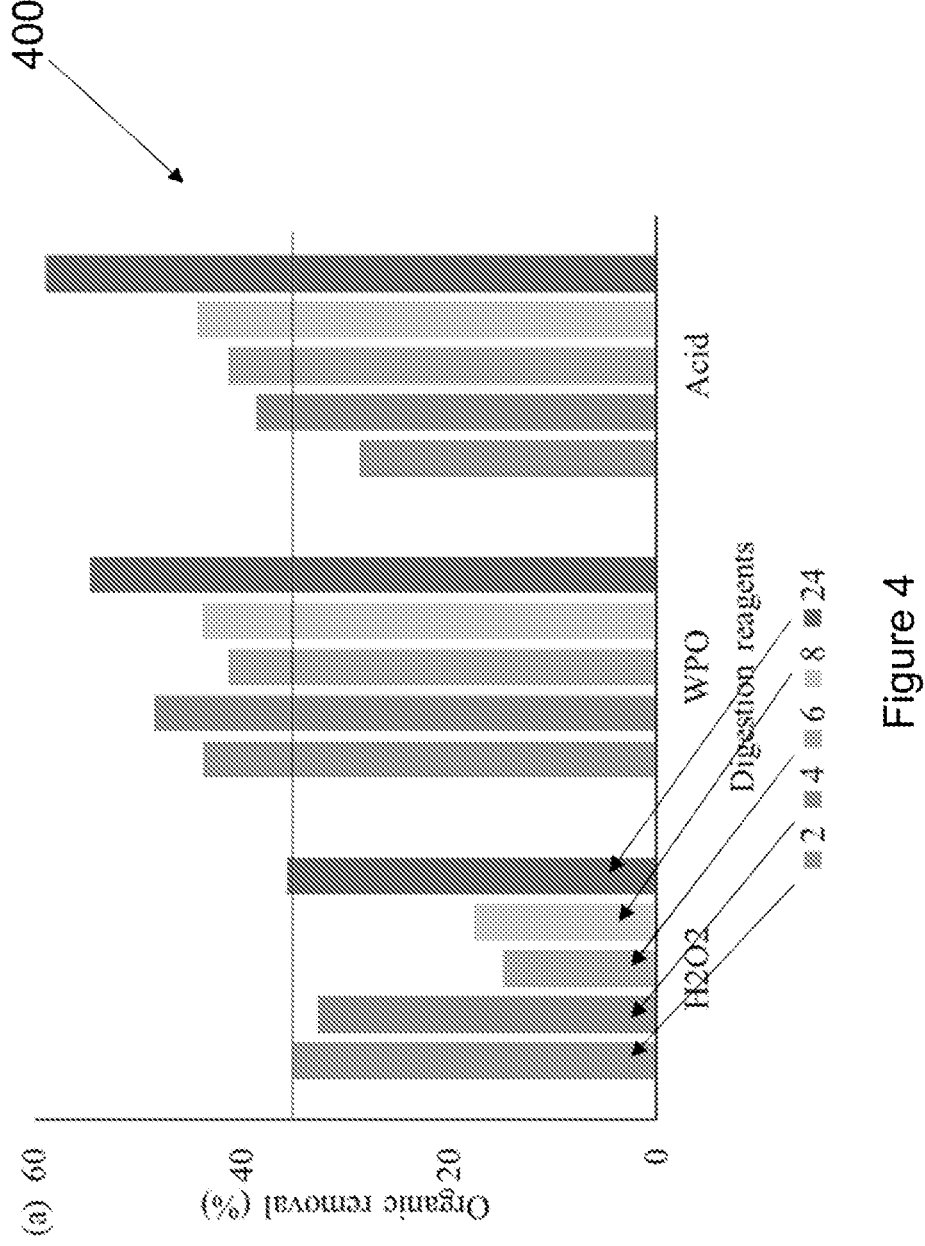
FIG. 4 is a graph showing percentage of non-microplastic organic matter removal when using different digestion reagents for different digestion durations in accordance with an example embodiment.
Figure 5:
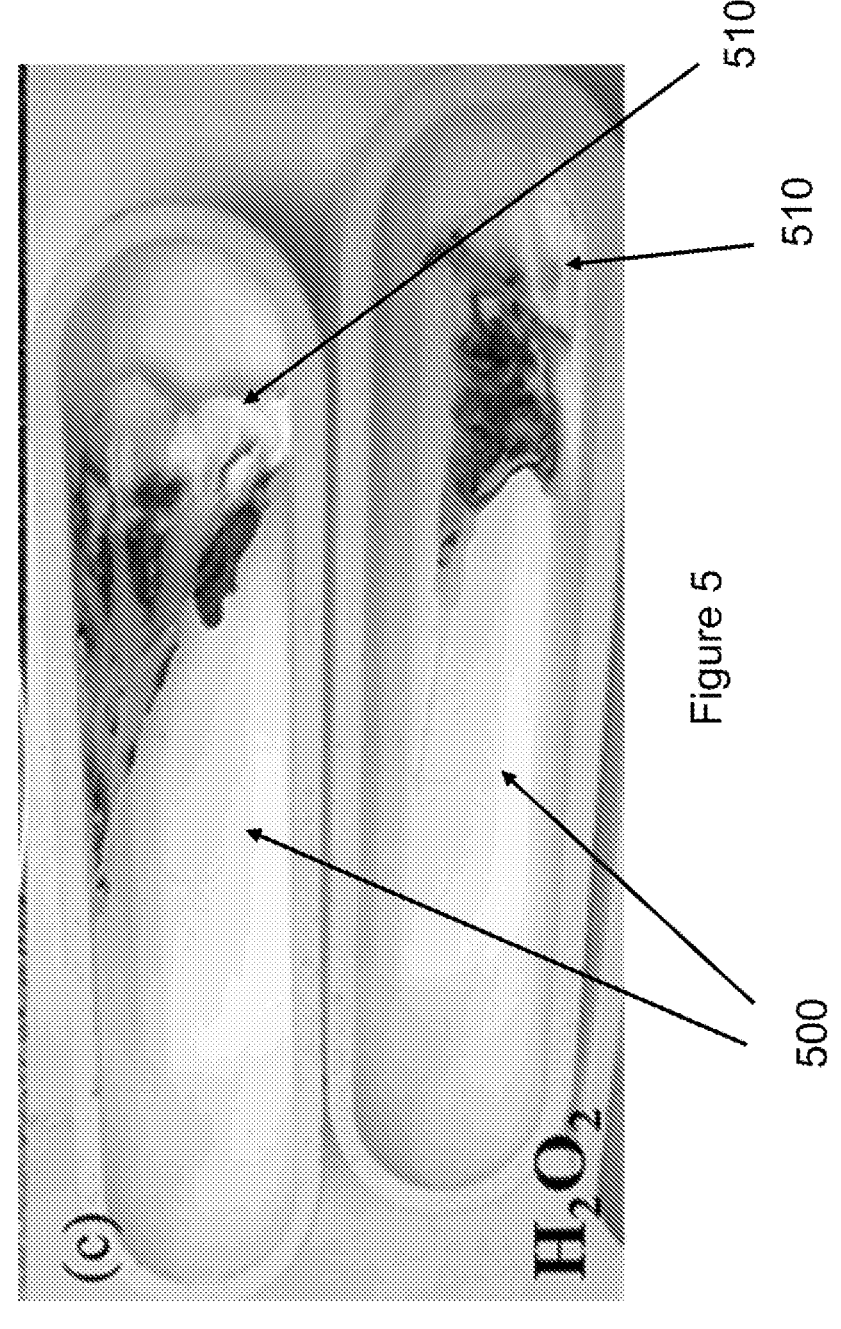
FIG. 5 is a photograph showing a filter with the captured microplastic polymer after total organic carbon (TOC) analysis of a hydrogen peroxide-digested pre-treated sample composition in accordance with an example embodiment.

In the digestion step 200, the sample composition is digested using a pre-determined digestion reagent for a pre-determined digestion duration to remove all non-microplastic organic matter 710. The digestion reagents include 30% hydrogen peroxide, wet peroxide oxidation (WPO) (i.e., 1:1 (v:v) 0.5 M Iron (II) to 30% Hydrogen Peroxide), a mixture of acids (i.e., 4:1 (v:v) 69% nitric acid to 70% perchloric acid). Experiments of samples with different polymer types in powder form, namely polyamide 66 (PA66), polyethylene (PE), polyethylene terephthalate (PET), polypropylene (PP), and polystyrene (PS), were conducted to test the digestion reagents and to determine digestion effectiveness and their effects on the recovery rate of polymer mass. FIG. 4 is a graph 400 illustrating the non-microplastic organic matter removal efficiency when hydrogen peroxide, WPO and a mixture of acids was used and shows that all the digestion reagents were effective in removing non-microplastic organic matter under digestion. In a preferred embodiment the digestion reagent 320 used may be hydrogen peroxide and a mixture of acids. In a most preferred embodiment, the digestion reagent includes 30% hydrogen peroxide, as shown in FIGS. 3A, 3B and 5.

Preferably, the pre-determined digestion duration is between 2 hours to 24 hours. Synthetic sludge samples with microplastics present were prepared to investigate the effects of different digestion durations on the removal efficiency of non-microplastic organic matter/impurities 730 in the samples. Digestion durations of 2 hours to 24 hours achieved high removal efficiency as shown in FIG. 4 whereby pre-determined digestion durations of 2 hours, 4 hours, 6 hours, 8 hours and 24 hours achieved high non-microplastic organic removal efficiency. In a preferred embodiment, the pre-determined digestion duration is 2 hours, 4 hours, 6 hours, 8 hours or 24 hours. In a most preferred embodiment, the pre-determined digestion duration is 2 hours and the digestion reagent may be 30% hydrogen peroxide, and digestion 200 of the sample composition is performed on a heat plate 740 at a temperature of 45° C. for 2 hours and the sample composition is stirred at a rate of 200-300 rotations per minute using a stirring means 750.

In the extraction step 210, the microplastic polymer is extracted from the sample composition by density separation 720 to produce a microplastic layer 710. This is, for example, done using a separation funnel 720 whereby a separation reagent is added to the sample composition. The ratio of sample to separation reagent is 1:1 for a sample with low organic content. The ratio of sample to separation reagent is 1:3 for an organic-rich or solid-rich sample. Preferably, the separation reagent is filtered sodium bromide and the density separation is performed at 25° C. for at least 2 hours with settled solids 730 at the bottom of the separation funnel drained and discarded every 30 minutes and the density separation completed when there is no settlement of solids observed.

Figure 3A:
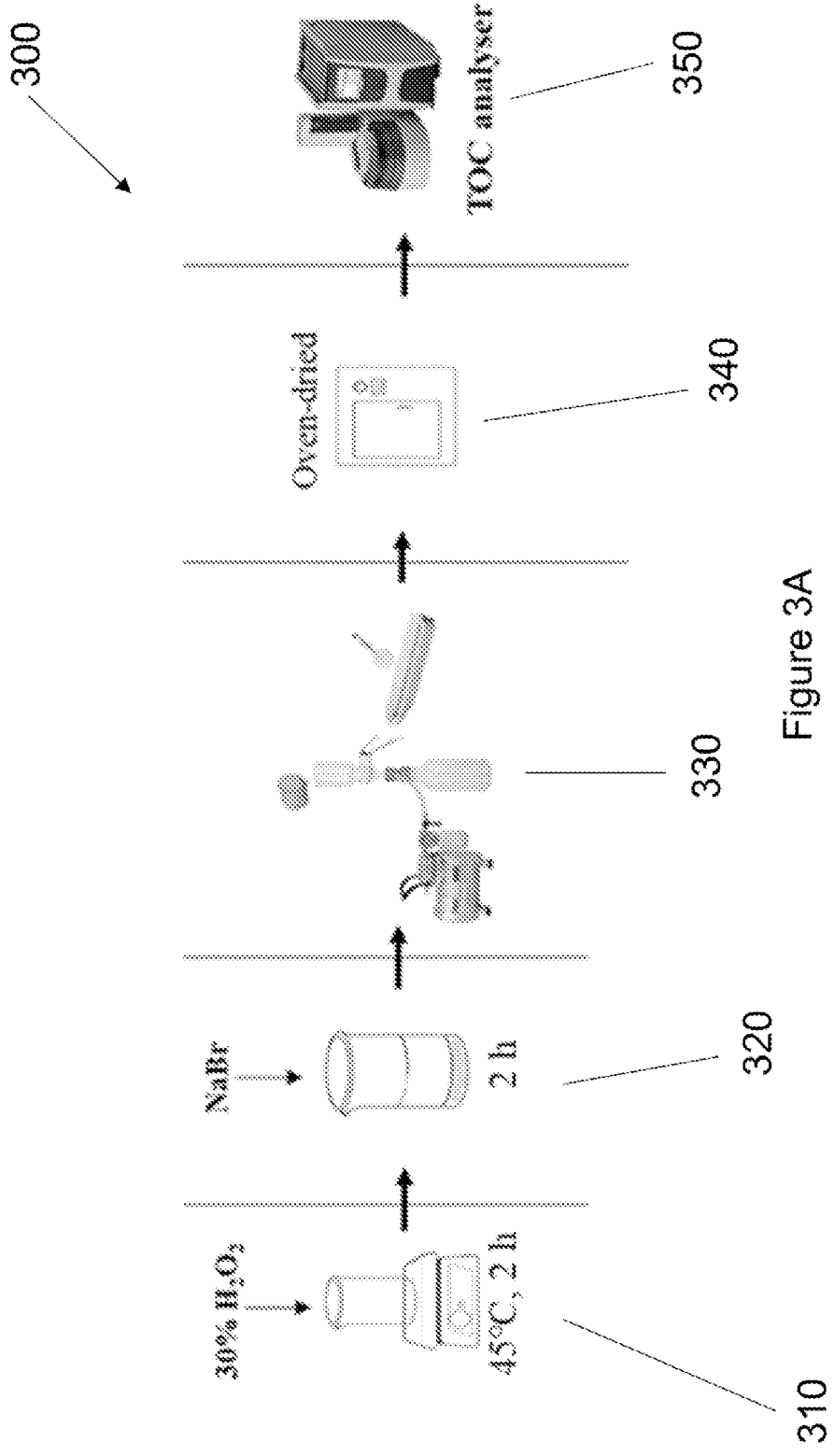
FIG. 3A is a schematic showing a method of quantifying microplastic mass in a sample composition with low organic content in accordance with an example embodiment.
Figure 3B:
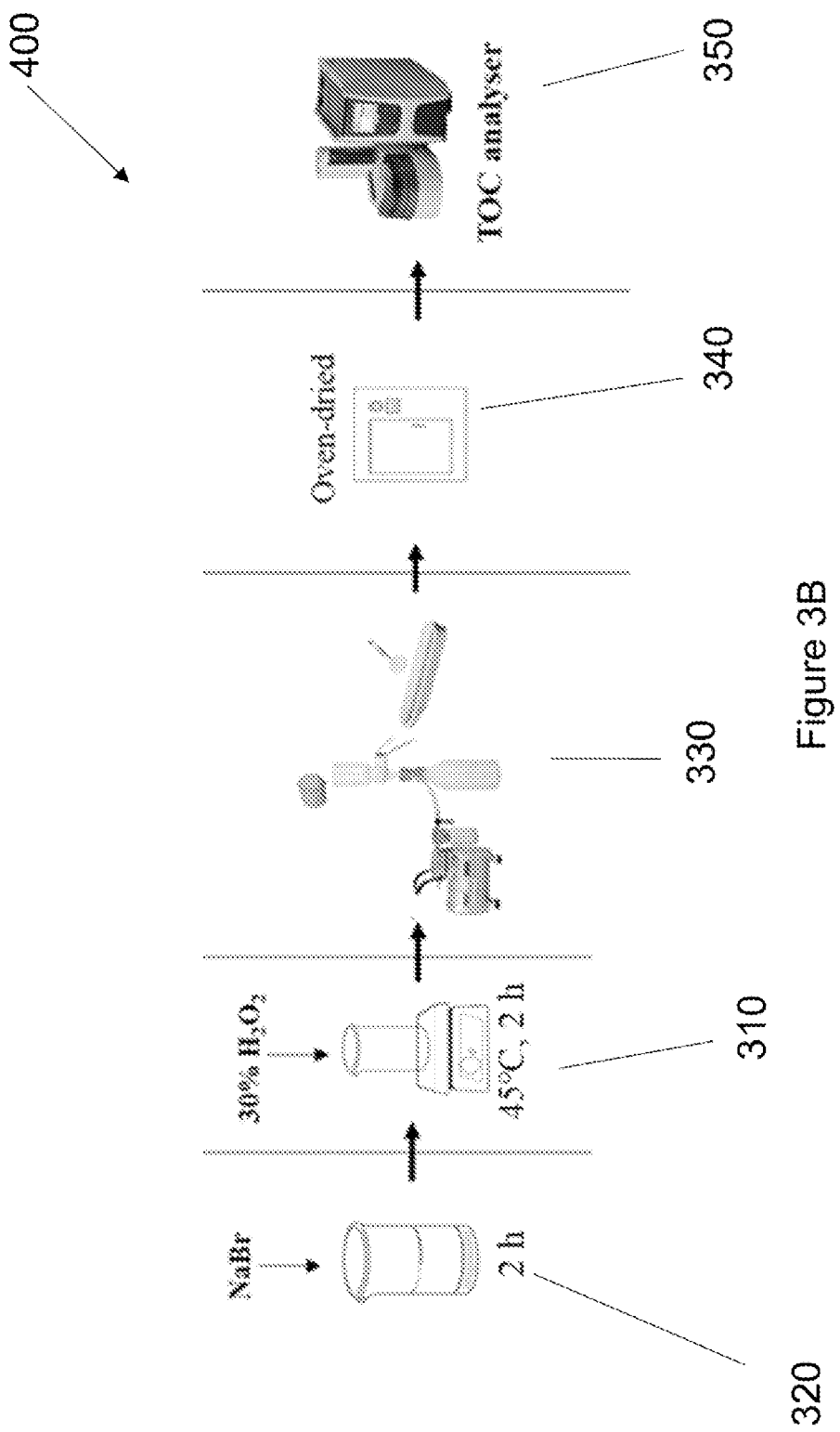
FIG. 3B is a schematic showing a method of quantifying microplastic mass in a sample composition with high organic content in accordance with an example embodiment.

With reference to FIGS. 3A and 3B, the sample pre-treatment includes two operation modes, a second operation mode 300 for sample compositions with low organic content as illustrated in FIG. 3A, and a first operation mode 400 for sample compositions with high organic content as illustrated in FIG. 3B.

With reference to FIG. 3B, in the first operation mode 400, for sample compositions with high organic content/, microplastics need to be isolated or separated from the sample composition via density separation 320 first at room temperature for 2 hours using a separation agent of sodium bromide solution. The density separation 320 process is shown in FIG. 7A in which a separation funnel 720 is used for density separation 320. After density separation, the solid layer 730, containing the non-microplastic organic matter/solids/impurities, is discarded. Digestion 310 is then carried out whereby digestion reagent is added to the microplastic layer 710 and a heat plate 740 and stirring means 750 is used to stir the sample composition at 200 rotations per minute at 45° C. for 2 hours. FIG. 7B illustrates the sample composition before digestion and FIG. 7C illustrates the sample composition after 2-hour digestion. Filtration 330 followed by drying 340 and TOC analysis 350 is then performed. The first operation mode achieved a high recovery rate of microplastic polymer mass at 102.3%. The superiority of utilising the first operation mode 400 for a sample composition with a high organic content is illustrated in FIG. 7D that shows an experiment conducted that used a sample composition with high organic content in which the polymer mass recovery rate was significantly higher when density separation 320 was conducted before digestion 310 during sample pre-treatment.

With reference to FIG. 3A, in the second operation mode 300, for sample compositions with low organic contents, during pre-treatment the sample composition undergoes digestion 310 followed by density separation 320. After density separation 320 the sample undergoes filtration 330, drying 340 and TOC analysis 350. The second operation mode is suitable for removal of non-microplastic organic matter in sample compositions with low organic content. In an alternative embodiment, the pre-determined digestion duration and the density separation duration is 0.5 hours to 1 hour each depending on the organic removal efficiency and settling rate.

The first 400 and second 300 operation modes were tested using sludge (high organic content) and water (low organic content) samples, respectively, and advantageously showed high recovery rates for synthetic and real wastewater and sludge samples with different microplastic polymer compositions.

After digestion 200 and density separation 210 are complete, the microplastic layer containing microplastic polymers is filtered 220 such that the microplastic polymer is captured in the filter 330. The filter is a 0.4-μm glass fiber filter, and the filtration is conducted under vacuum.

With reference to FIGS. 6A and 6B, following filtration 220, the filter with the captured microplastic polymer 510 is put in a pre-treated ceramic boat 500 and dried 230 for a pre-determined drying time at a pre-determined drying temperature in an oven in preparation for TOC analysis 350. In a preferred embodiment, the pre-determined drying time is between 2 hours and 8 hours and the pre-determined drying temperature is 60° C. As shown in FIG. 6A, incomplete combustion was found at the filters 510 in ceramic boats 500 when the drying step 230 was omitted and wet filters 510 were used directly after 2-hour digestion 200. The presence of residues and incomplete combustion after TOC analysis 350 was significantly reduced in dried filters 515 as shown in FIG. 6B. Thus, it was found that the dryness of the digested samples had an effect on the combustion efficiency and consequently the accuracy of the TOC analysis 350. Accordingly, the drying step 230 was adopted in which the filters 510 were dried in an oven at 60° C. for 2 hours to ensure accuracy of the TOC analysis 350.

Total organic carbon (TOC) analysis 110 is performed using a TOC analyzer 350 and the microplastic mass in the sample composition is quantified according to the organic carbon content of the microplastic polymer. The pre-treated sample composition is inserted into the TOC analyzer 350 and combusted at 900° C. to measure the carbon mass of the microplastic polymer. The microplastic mass is calculated using the following equation:

$$MP_M = \frac{TOC_C}{P_C}$$

where $MP_M$ is the mass of microplastics, $P_C$ is the carbon content of the associated plastic types, and $TOC_C$ is the measured carbon mass from the TOC analyzer 350.

The claimed invention beneficially provides an inexpensive and effective method of monitoring and measuring microplastic mass by utilising equipment largely available in environmental testing laboratories in place of more costly instruments and less accurate analytical techniques to target emerging pollutants in the environment. The claimed method enables fast detection of microplastics in sample compositions with varying viscosities, like water or sludge, using existing infrastructure.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

The experiments as described below provide further examples of the invention as claimed as an effective, reliable, and accurate means of quantifying microplastic mass in a sample composition.

EXAMPLES

Example 1

Selection of Digestion Reagent

Purchased samples with different polymer types in powder form, namely polyamide 66 (PA66), polyethylene (PE), polyethylene terephthalate (PET), polypropylene (PP), and polystyrene (PS), were considered for the experiment of different digestion reagents. In the preliminary stage, digestion reagents of (1) 30% hydrogen peroxide, (2) wet peroxide oxidation (WPO) (i.e., 1:1 (v:v) 0.5 M Iron (II) to 30% hydrogen peroxide), and (3) mixture of acids (i.e., 4:1 (v:v) 69% nitric acid to 70% Perchloric acid) were selected to determine the digestion effectiveness and their effects on the recovery rate of polymer mass (FIG. 4). While all the tested digestion reagents were effective in removing non-microplastic organic matter, hydrogen peroxide and acid digestion were most cost-effective.

Selection of Digestion Duration

Incomplete digestion was observed when the residues in a ceramic boat appeared black (FIG. 5). Synthetic sludge samples with the presence of microplastics were prepared to investigate the effects of different digestion durations, i.e., 2 hours-24 hours, on the removal efficiency of the non-microplastic organic matter samples. All the digestion durations were effective and achieved high removal. Considering the cost-effectiveness of the pre-treatment process, the use of hydrogen peroxide for 2 hours was selected.

Selection of Drying Temperature

Incomplete combustion was found at the residues in ceramic boats (FIG. 6A). Since the filters in ceramic boats remained wet after 2-hour digestion, the dryness of digested samples might affect the combustion efficiency and thus the accuracy of the TOC analysis. Drying in the oven at 60° C. for 2 hours to 8 hours was practiced. Fewer black residues were found in a ceramic boat after TOC analysis, showing that an extra drying step should be adopted before TOC analysis (FIG. 6B).

Operation Modes for Samples with High Organic Content vs Samples with Low Organic Content For samples with low organic contents, the durations of digestion and density separation may be shortened to 0.5 hours to 1 hour each, depending on the organic removal efficiency and settling rate. Based on the modified protocol, different synthetic samples were prepared to investigate the feasibility of TOC analysis for microplastic quantification. Different microplastic polymer types in pellet and powder forms were used to examine the reliability of the proposed protocol. However, for the samples with high organic contents, hydrogen peroxide-digestion might not be enough to remove most organic contents, which would affect the accuracy of the proposed protocol for microplastic quantification. Besides, a foam layer was present, and the semi-digested particles affected the separation efficiency. Isolation of microplastics from samples is the first priority of mass quantification using this technique. Thus, the microplastic extraction procedure was further revised to separate microplastics from samples first and remove the organic matter in the separated samples. 200 mL of Sodium bromide solution was added to the samples for density separation at room temperature for 2 hours. An obvious solid layer was found and discarded. 200 ml of 30% hydrogen peroxide solution was added to 200 mL of separated samples. The heat plate stirrer was operated at 200 rotations per minute (rpm) and 45° C. for 2 hours. After 2-hour digestion, the digested samples were filtered through a 0.4 μm glass fiber filter under vacuum. 200 mL of synthetic water with high organic contents was collected to examine the difference in recovery rate between the original and modified protocols. The modified protocol (for samples with high organic content) achieved higher recovery rates of polymer mass at 102.3%.

Sample Pre-Treatment

Digestion

Non-microplastics organic matter was removed from the samples. 200 mL of the collected sample was transferred to a 600-mL beaker, and 200 mL of 30% filtered hydrogen peroxide was added to the beaker accordingly. The ratio of the sample with low organic content to digestion reagent was 1:1, while the ratio of the sample with high organic content to digestion reagent was 1:2. The digestion was performed on a heat plate with the stirring rate at 200-300 rpm and 45° C. for 2 hours.

If the non-microplastic organic matter was visible or the digested sample was not clear enough, the digestion was extended and more 30% filtered hydrogen peroxide solution (i.e., 50 mL) was added until complete digestion occurred. The digestion was completed when the sample was completely clear after settling and with no bubble layer on the surface.

Density Separation

After removing non-microplastic organic matter, microplastics were extracted from the digested sample. The digested sample was transferred to a 500-mL separation funnel, and filtered sodium bromide solution was added gently. The ratio of sample with low organic content to separation reagent was 1:1, while the ratio of sample with high organic content or solid-rich sample to separation reagent was 1:3. The density separation was performed at room temperature (i.e., 25° C.) for at least 2 hours. The settled solids at the bottom of the separation funnel were drained and discarded every 30 minutes. If there were visible solids in the middle of the separation funnel, an extra 50 mL of filtered sodium bromide solution was gently added to the digested samples. The density separation was completed when there was no other settlement after adding extra sodium bromide solution.

Filtration

The upper layer was filtered through a 0.4-μm glass fiber filter under vacuum.

Drying

After filtration, the filter was put in a pre-treated ceramic boat and dried in an oven at 60° C. overnight (i.e., 2 hours to 8 hours).

TOC Analysis

Glucose with 40% carbon content was used to develop the calibration curve of TOC analysis. Glucose was weighed at 0.5 mg, 1 mg, 25 mg, 50 mg, and 75 mg by 5-digit balance. The weighed glucose was put in the pre-treated ceramic boat and injected into a TOC analyzer with a solid-sample combustion unit to develop a calibration curve. After the development of the calibration curve, the filter-containing ceramic boat was injected into a TOC analyzer with a solid-sample combustion unit. The sample was combusted at 900° C. to measure the carbon content. The microplastic mass was calculated following Equation 1.

$$MP_M = \frac{TOC_C}{P_C} \qquad \text{Equation 1}$$

where $MP_M$ was the mass of microplastics, $P_C$ was the carbon content of the associated plastic types, and $TOC_C$ was the measured carbon mass from the TOC analyzer.

Experimental Results

Table 1 below shows organic removal (%) under different digestion reagents and digestion duration

|  | 2 hours | 4 hours | 6 hours | 8 hours | 24 hours |
|---|---|---|---|---|---|
| 30% Hydrogen peroxide | 35.0% | 32.6% | 14.7% | 17.6% | 35.6% |
| WPO | 43.6% | 48.4% | 41.3% | 43.8% | 54.6% |
| Acid | 28.6% | 38.6% | 41.2% | 44.1% | 58.9% |

Table 2 below shows preliminary results of microplastic quantification in purchased polymer and synthetic sludge samples using TOC analyzer

|  | PA66 | PE | PET | PP | PS |
|---|---|---|---|---|---|
| Carbon content (%) | 63.7 | 85.7 | 62.5 | 85.7 | 92.3 |
| Mass concentration of purchased polymer in powder form (n = 3) (FIG. 8A) | | | | | |
| Added polymer mass (mg) | 50.3 | 50.2 | 50.4 | 50.1 | 50.2 |
| Total carbon mass (mg) | 29.9 | 41.5 | 30.1 | 43.8 | 43.5 |
| Calculated polymer mass (mg) | 47.0 | 48.5 | 48.1 | 51.2 | 47.2 |
| Recovery rate ( %) | 93.4 | 96.5 | 95.6 | 102.2 | 93.9 |
| Mass concentration of purchased polymer in pellet form (n = 3) (FIG. 8B) | | | | | |
| Added polymer mass (mg) | 50.0 | 46.8 | 48.0 | 55.0 | / |
| Total carbon mass (mg) | 29.7 | 39.7 | 28.8 | 46.6 | / |
| Calculated polymer mass (mg) | 46.7 | 46.3 | 46.0 | 54.3 | / |
| Recovery rate (%) | 93.4 | 98.9 | 95.9 | 98.7 | / |
| Mass concentration of synthetic liquid samples with purchased polymer in powder form (n = 3) (FIG. 8C) | | | | | |
| Added polymer mass (mg) | 250.2 | 250.1 | 250.2 | 250.0 | 250.1 |
| Total carbon mass (mg) | 118.1 | 122.4 | 137.0 | 17.7 | 198.4 |
| Calculated polymer mass (mg) | 185.4 | 142.8 | 219.2 | 20.6 | 215.0 |
| Recovery rate (%) | 74.1 | 57.1 | 87.6 | 8.2 | 85.9 |

-continued

|  | PA66 | PE | PET | PP | PS |
|---|---|---|---|---|---|
| Mass concentration of pond water samples with purchased polymer in powder form (n = 3) (FIG. 8D) | | | | | |
| Added polymer mass (mg) | 10.0 | 10.0 | 10.1 | 10.0 | 10.1 |
| Total carbon mass (mg) | 6.0 | 8.3 | 6.6 | 7.7 | 8.1 |
| Calculated polymer mass (mg) | 9.5 | 9.6 | 10.6 | 8.9 | 8.7 |
| Recovery rate ( %) | 94.4 | 96.1 | 105.0 | 89.5 | 86.2 |
| Mass concentration of pond water samples with purchased polymer in pellet form (n = 3) (FIG. 8E) | | | | | |
| Added polymer mass (mg) | 54.9 | 52.8 | 60.4 | 55.5 | / |
| Total carbon mass (mg) | 35.9 | 46.7 | 39.4 | 47.7 | / |
| Calculated polymer mass (mg) | 56.4 | 54.5 | 63.0 | 55.7 | / |
| Recovery rate (%) | 102.6 | 103.2 | 104.4 | 100.3 | / |
| Mass concentration of synthetic sludge samples with purchased polymer in powder form (n = 3) (FIG. 8F) | | | | | |
| Added polymer mass (mg) | 10.2 | 10.0 | 10.0 | 10.3 | 10.2 |
| Total carbon mass (mg) | 8.8 | 8.2 | 7.1 | 10.5 | 8.1 |
| Calculated polymer mass (mg) | 13.8 | 9.5 | 11.4 | 12.2 | 8.7 |
| Recovery rate ( %) | 134.5 | 95.7 | 114.5 | 119.1 | 85.6 |
| Mass concentration of dewatered sludge from Tai Po Water Treatment Works (TPWTWs) with purchased polymer in powder form (n = 3) (FIG. 8G) | | | | | |
| Added polymer mass (mg) | 10.0 | 10.0 | 10.0 | 10.0 | 10.0 |
| Total carbon mass (mg) | 14.4 | 16.6 | 14.4 | 18.1 | 17.0 |
| Calculated polymer mass (mg) | 9.7 | 9.8 | 9.9 | 11.5 | 9.5 |
| Recovery rate (%) | 97.7 | 98.3 | 99.5 | 115.9 | 95.5 |
| Mass concentration of dewatered sludge from TPWTWs with purchased polymer in pellet form (n = 3) (FIG. 8H) | | | | | |
| Added polymer mass (mg) | 55.1 | 54.4 | 60.1 | 57.2 | / |
| Total carbon mass (mg) | 40.4 | 53.9 | 44.9 | 56.3 | / |
| Calculated polymer mass (mg) | 50.6 | 53.3 | 58.8 | 56.2 | / |
| Recovery rate ( %) | 91.8 | 97.9 | 97.8 | 98.1 | / |

Table 3 below shows preliminary results of microplastic quantification in mixed polymer samples (n=3) (FIG. 8I) using TOC analyzer

|  | Mixed sample A | Mixed sample B | Mixed sample C |
|---|---|---|---|
| Added polymer mass (mg) | 25.0 | 25.0 | 24.9 |
| Calculated polymer mass (mg) | 24.9 | 24.5 | 24.9 |
| Recovery rate ( %) | 99.5 | 98.1 | 100.0 |

As shown in Table 2, experimental results showed a high recovery rate of polymer types in powder (i.e., 93.4%-102.2%) and pellet (i.e., 93.4%-98.9%) forms (FIGS. 8A and 8B). 200 mL of pond water with 55 mg of different microplastic pellets (i.e., PA66, PE, PET, and PP) or 10 mg of different microplastic powders (i.e., PA66, PE, PET, PP, and PS) were added and prepared as pond water samples. Upon experiment modification, outstanding recovery rates of microplastic mass were obtained in the pond water samples in powder (i.e., 86.2%-105.0%) and pellet (i.e., 100.3%-104.4%) forms (FIGS. 8D and 8E).

100 mg of sludge with the addition of 10 mg of different microplastic polymers (i.e., PA66, PE, PET, PP, and PS) in powder form were prepared as synthetic sludge samples. High recovery rates from 85.6% to 134.5% were achieved in the synthetic sludge samples (FIG. 8F). With the outstanding recovery rate of polymer mass in synthetic sludge samples, microplastic quantification of dewatered sludge from Tai Po Water Treatment Works (TPWTWs) was examined based on the design of the experiment. Approximately 55 mg of different microplastic pellets (i.e., PA66, PE, PET, and PP) or 10 mg of different microplastic powders (i.e., PA66, PE, PET, PP, and PS) were spiked in 100 mg of dewatered sludge from Tai Po Water Treatment Works (TPWTWs). Through using real samples to verify the reliability of the modified protocols, outstanding recovery rates of microplastic mass were obtained in the dewatered sludge samples in powder (i.e., 97.7%-115.9%) and pellet (i.e., 91.8%-98.1%) forms (FIGS. 8G and 8H). Results showed that the calculated mass concentrations of different microplastic polymer types had similar values to the added microplastic mass concentrations, demonstrating that the developed TOC-based method is suitable for the microplastic quantification of both liquid and sludge samples (Table 2).

The microplastic quantification of previous experiments was based on a single polymer in powder or pellet forms. However, microplastic polymers exist in various compositions in the real situation. With the successful application of the quantification of a single polymer, the feasibility of TOC analysis for microplastic quantification for samples with mixed polymers was investigated. For purchased polymer samples, three unknown compositions of different microplastic polymer types in powder forms were prepared to verify the reliability of the proposed protocol. The experimental results showed a high recovery rate of polymer mass in powder (i.e., 98.1-100.0) (FIG. 8I and Table 3).

The invention claimed is:

1. A method of quantifying a total microplastic mass in a sample composition, the method comprising:
    providing a treated sample composition by removing non-microplastic organic matter from the sample composition and by extracting a microplastic polymer having an organic carbon content from the sample composition,
    measuring the organic carbon content of the extracted microplastic polymer in the treated sample composition by using total organic carbon (TOC) analysis, and
    quantifying the total microplastic mass in the sample composition based on the measured organic carbon content of the extracted microplastic polymer.

2. The method according to claim 1, wherein the removing the non-microplastic organic matter from the sample composition comprises digesting the sample composition using a digestion reagent for a pre-determined digestion duration, the extracting the microplastic polymer from the sample composition comprises producing a microplastic layer by using density separation, and the providing the treated sample composition further comprises:
    capturing the microplastic polymer in a filter by filtering the microplastic layer through the filter, and drying the filter with the captured microplastic polymer for a pre-determined drying time at a pre-determined drying temperature prior to the total organic carbon (TOC) analysis.

3. The method according to claim 2, wherein the digestion reagent is selected from the group consisting of a 30% hydrogen peroxide solution, a wet peroxide oxidation (WPO) solution, and an acid solution.

4. The method according to claim 2, wherein the pre-determined digestion duration is between 2 and 24 hours.

5. The method according to claim 2, wherein the pre-determined digestion duration is 2, 4, 6, 8 or 24 hours.

6. The method according to claim 2, further comprising adding filtered sodium bromide before the extracting the microplastic polymer from the sample composition, and wherein the producing the microplastic layer by using density separation comprises maintaining the sample composition at 25° C. for at least 2 hours.

7. The method according to claim 2, wherein the filter is a glass fiber filter having pores of a 0.4-μm diameter.

8. The method according to claim 2, wherein the pre-determined drying time is between 2 and 8 hours and the pre-determined drying temperature is 60° C.

9. The method according to claim 2, the drying the filter with the capture microplastic further comprising putting the filter with the captured microplastic polymer inside a treated ceramic boat, putting the filter with the captured microplastic polymer inside an oven and drying the filter with the captured microplastic polymer inside the treated ceramic boat using the oven.

10. The method according to claim 1, wherein the total organic carbon (TOC) analysis comprises using a total organic carbon (TOC) analyzer.

11. The method according to claim 10, wherein the measuring the organic carbon content of the extracted microplastic polymer comprises inserting the treated sample composition into the TOC analyzer and combusting the treated sample composition at 900° C.

12. The method according to claim 1, wherein the extracted microplastic polymer is selected from the group consisting of polyamide 66 (PA66), polyethylene (PE), polyethylene terephthalate (PET), polypropylene (PP), and polystyrene (PS), or a combination thereof.

13. The method according to claim 1, wherein the extracted microplastic polymer is one or more extracted microplastic polymers.

14. The method according to claim 1, wherein the extracted microplastic polymer is in a powder form or in a pellet form.

15. The method according to claim 2, wherein the digesting the sample composition comprises maintaining the sample composition a temperature of 45° C. for 2 hours using a heat plate and stirring the sample composition at a rate of 200-300 rotations per minute.

16. The method according to claim 10, wherein the microplastic mass is quantified according to the carbon content of the microplastic polymer and a measured carbon mass from the TOC analyzer.

17. The method according to claim 1, wherein the sample composition is wastewater, pond water or sludge.

* * * * *